United States Patent [19]

Robertson

[11] Patent Number: 4,612,939

[45] Date of Patent: Sep. 23, 1986

[54] METHOD FOR DIAGNOSIS OF STRESS INCONTINENCE IN WOMEN

[76] Inventor: Jack R. Robertson, 1451 Refugio Rd., Santa Ynez, Calif. 93460

[21] Appl. No.: 661,087

[22] Filed: Oct. 15, 1984

[51] Int. Cl.⁴ ............................................. A61B 5/00
[52] U.S. Cl. .................................. 128/774; 128/782; 128/8; 604/54
[58] Field of Search ............................ 128/341–345, 128/748, 761, 774, 780, 782, 3–9; 604/54, 96–103

[56] References Cited

U.S. PATENT DOCUMENTS

| | | | |
|---|---|---|---|
| 2,687,131 | 8/1954 | Raiche | 604/101 |
| 3,421,509 | 1/1969 | Fiore | 128/343 X |
| 3,656,485 | 4/1972 | Robertson | 128/8 X |
| 3,709,214 | 1/1973 | Robertson | 128/4 |
| 4,072,144 | 2/1978 | Pelosi et al. | 128/774 |
| 4,148,319 | 4/1979 | Vasper et al. | 604/96 |
| 4,407,301 | 10/1983 | Streisinger | 128/774 |
| 4,434,797 | 3/1984 | Silander | 128/343 |
| 4,467,806 | 8/1984 | Bhiwandiwala | 128/341 |
| 4,484,585 | 11/1984 | Baier | 128/748 |
| 4,500,313 | 2/1985 | Young | 128/774 X |
| 4,538,621 | 9/1985 | Jarczyn | 129/748 |

Primary Examiner—Dalton L. Truluck
Attorney, Agent, or Firm—Romney Golant Martin Seldon & Ashen

[57] ABSTRACT

A tube is passed through the urethra into the bladder (indicated by liquid flow from the bladder to the distal end of the tube) and then withdrawn slightly so that its proximal end is within the urethra (indicated by flow cessation). The tube is anchored in that position by sliding a hygroscopic bougie up the outside of the tube and just inside the urethral meatus, and then spraying the bougie with water to expand it against the urethral wall. A proximal enlargement in the tube also aids anchoring.

A conical sheath is used to expand the meatus, to aid in inserting the tube and bougie. The patient holds a handle on the sheath to facilitate access to the meatus.

With the tube anchored, the patient undergoes stress of the type which produces the incontinence to be diagnosed, and the diagnostician observes the timing of liquid discharge from the urethra through the tube, relative to stress incidence. From this relative timing the type of incontinence is inferred. A second tube may be added for simultaneous measurement of bladder pressure.

11 Claims, 25 Drawing Figures

U.S. Patent  Sep. 23, 1986  Sheet 1 of 7  4,612,939
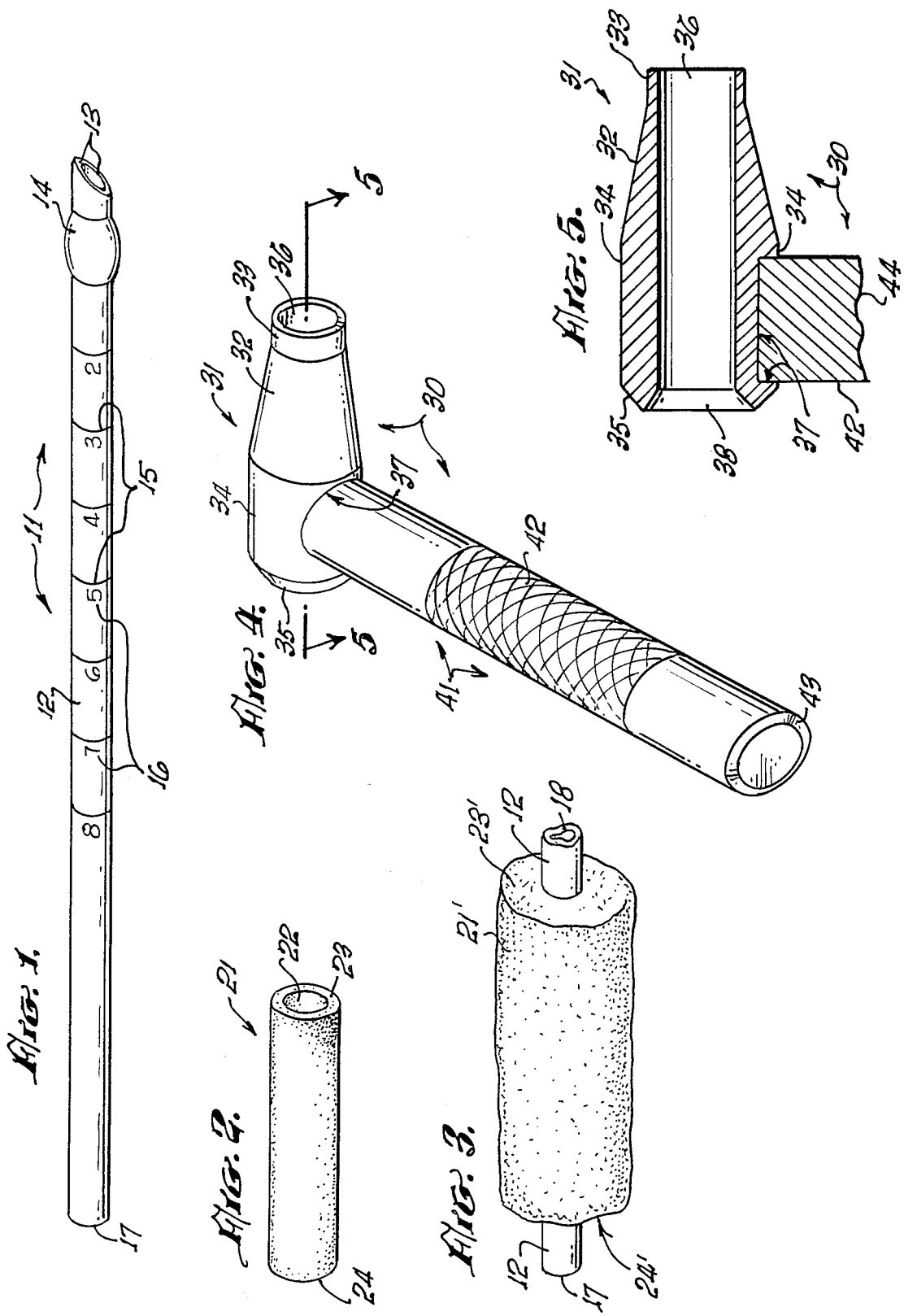

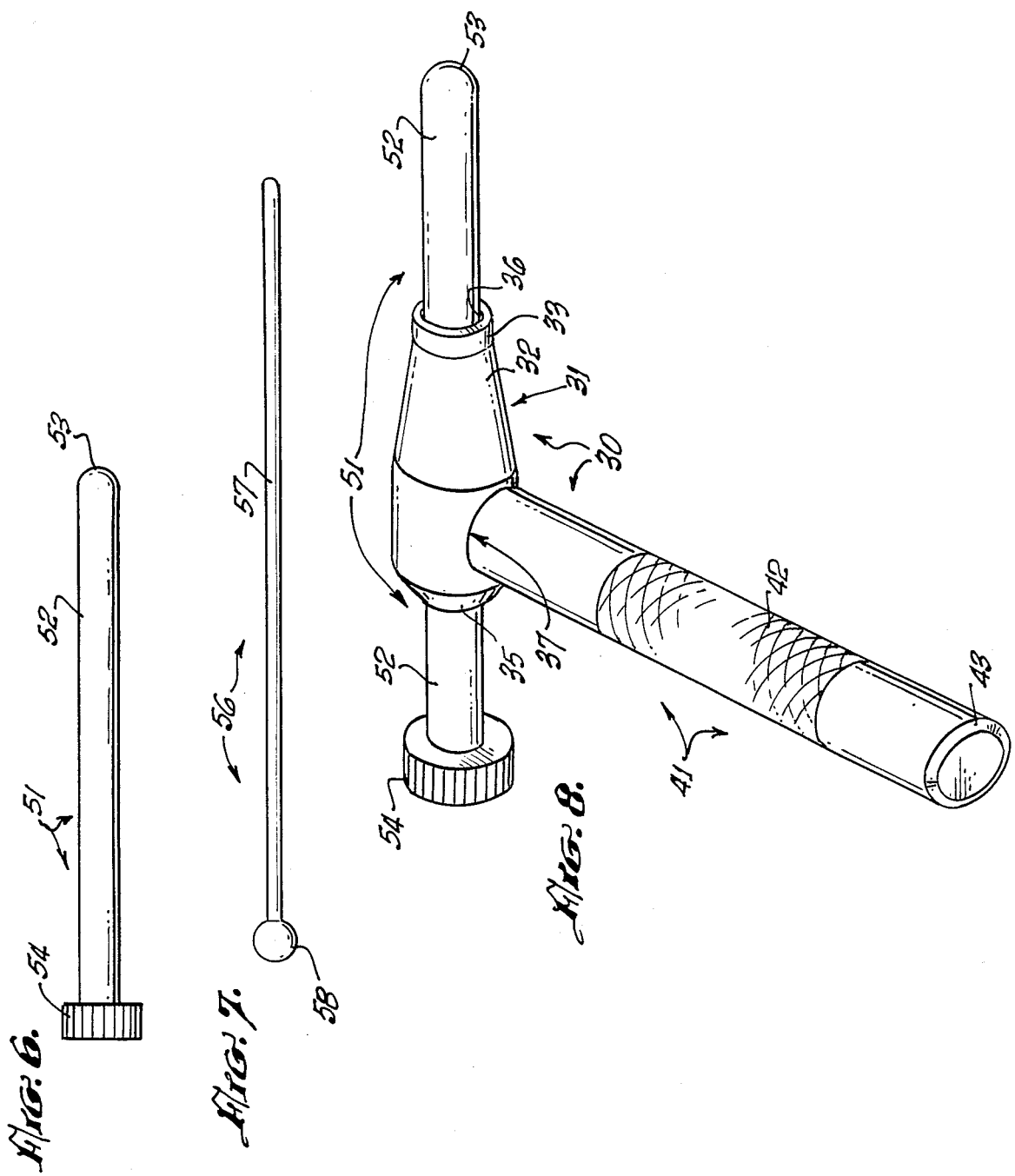

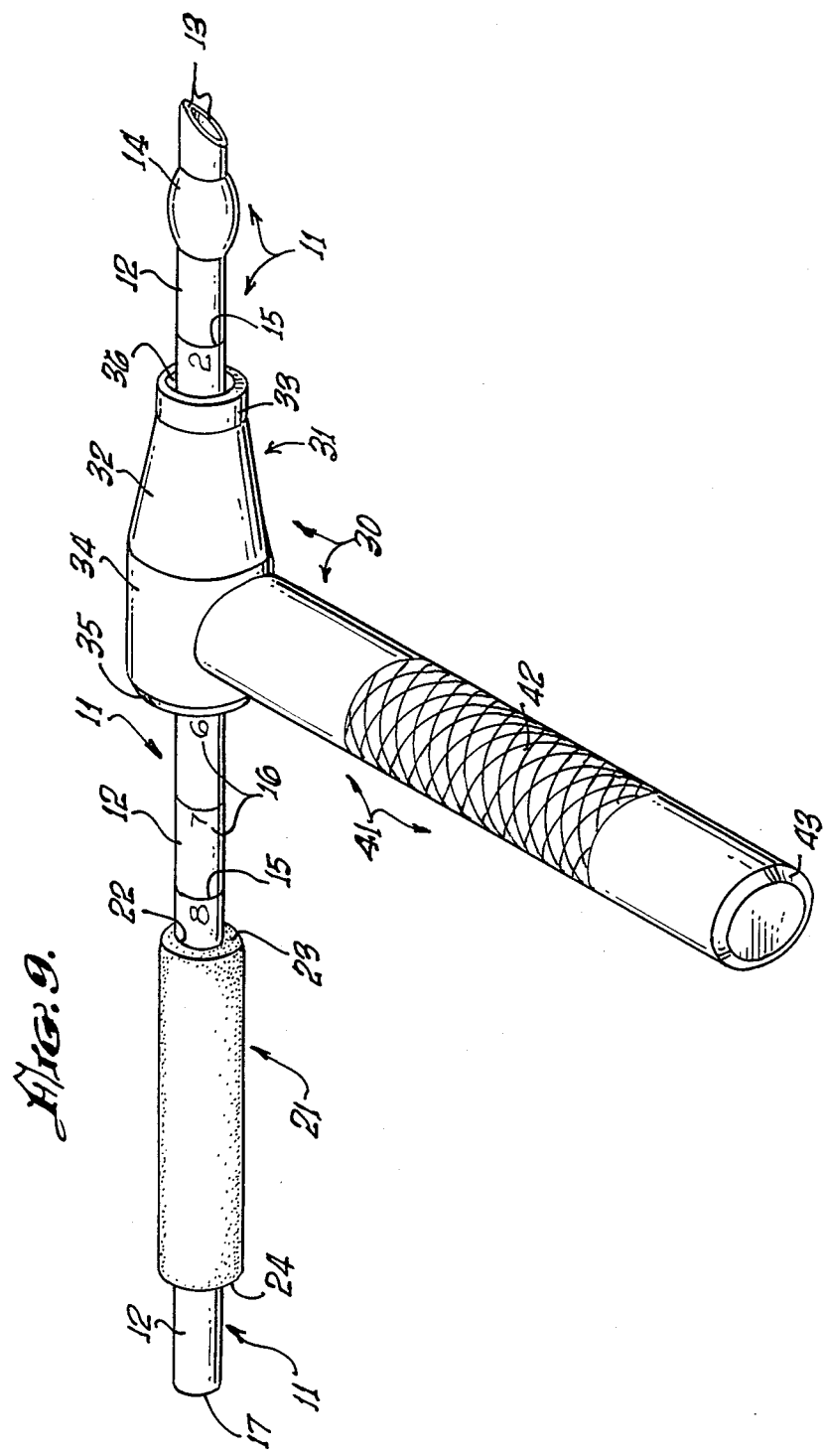

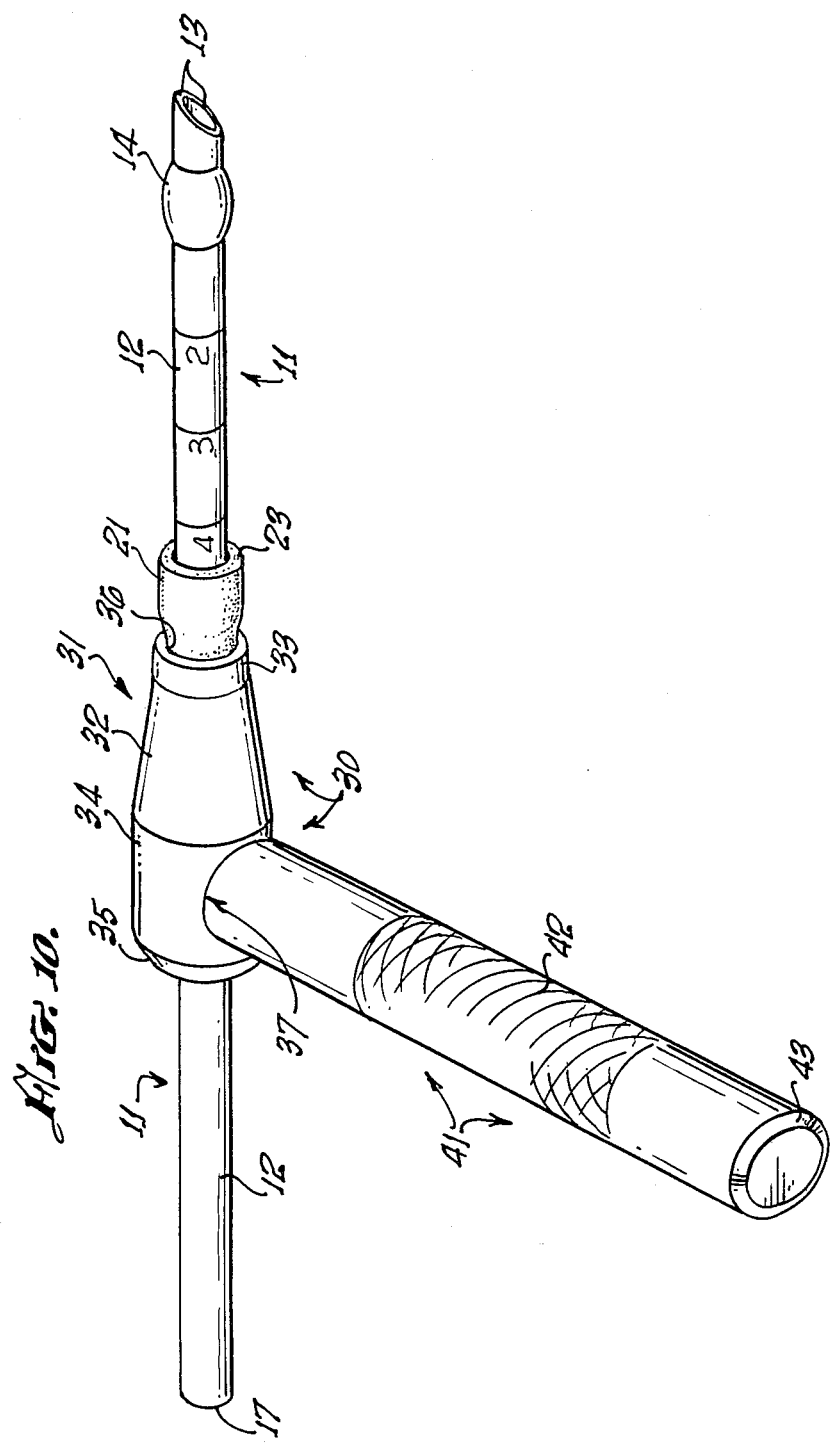

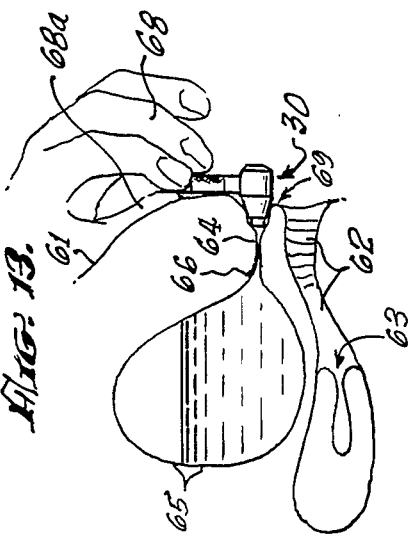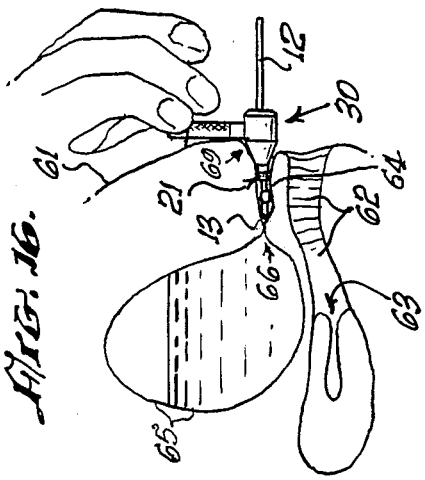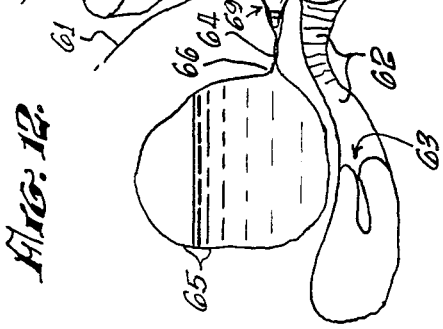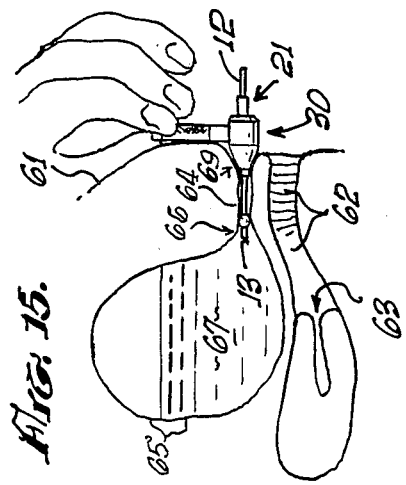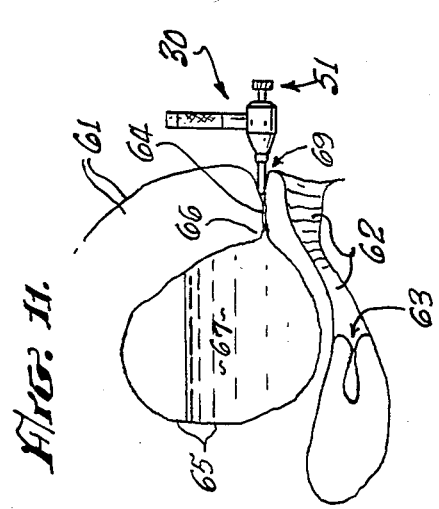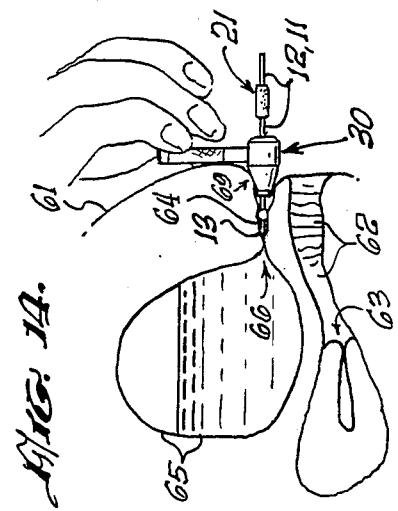

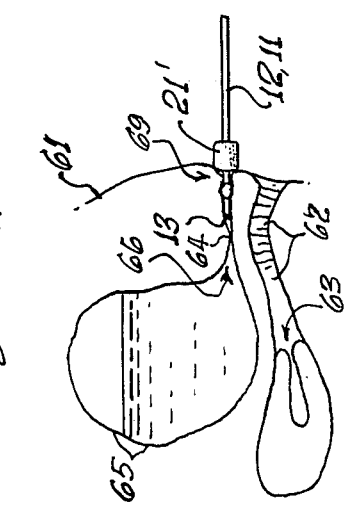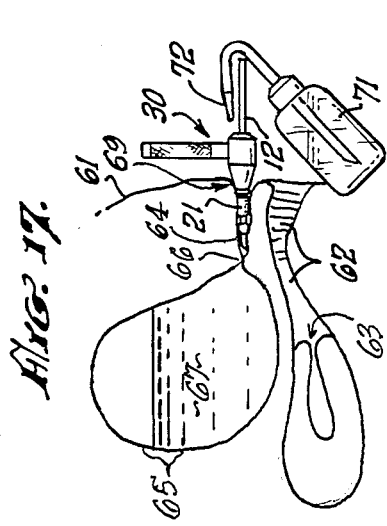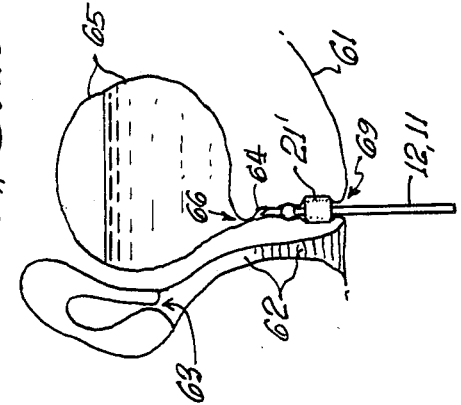

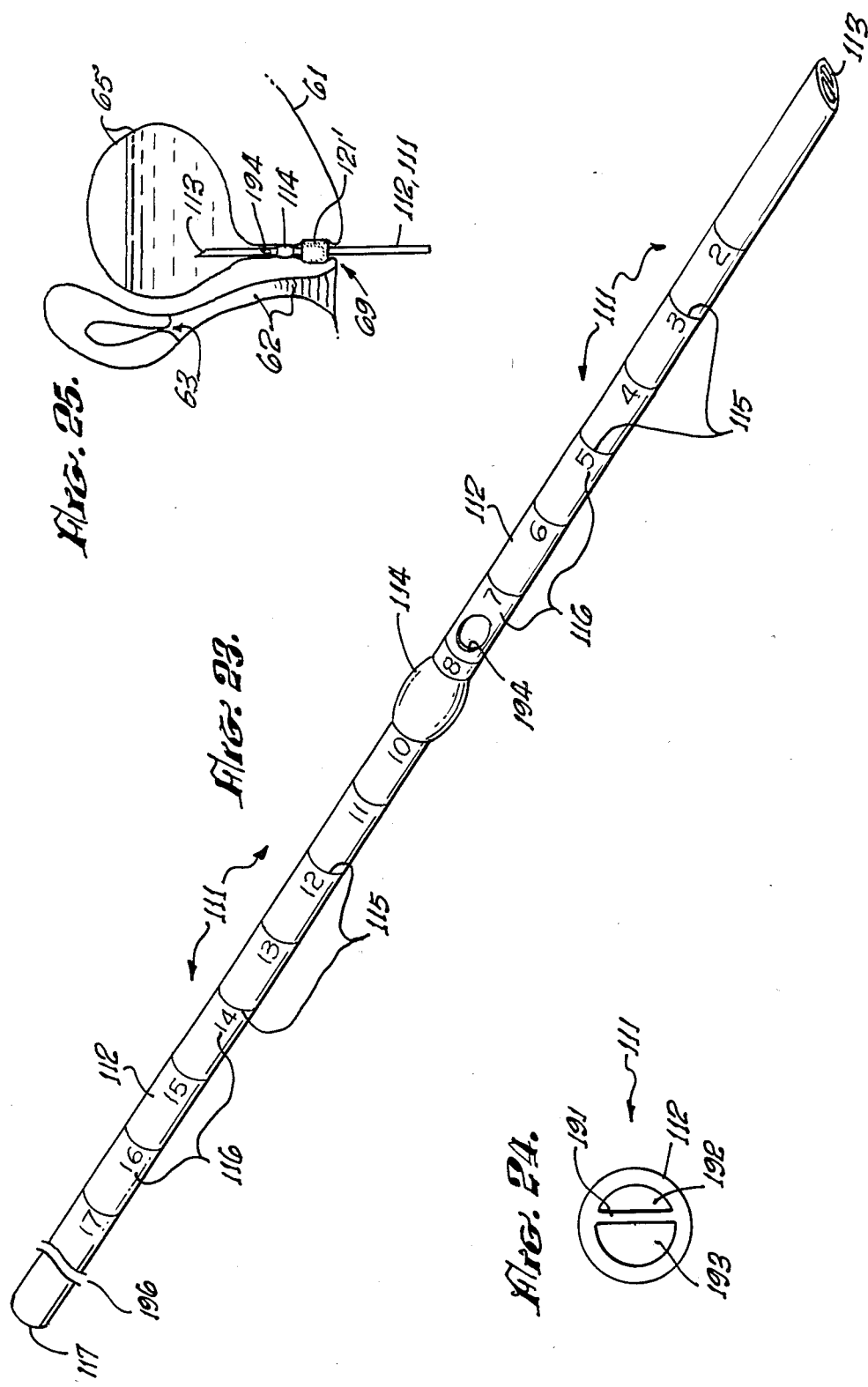

METHOD FOR DIAGNOSIS OF STRESS INCONTINENCE IN WOMEN

BACKGROUND

1. Field of the Invention

This invention relates generally to diagnostic apparatus and methods in gynecology, and more particularly to clinical diagnosis of stress incontinence.

2. Prior Art (a) Causes of Incontinence—Inability to deter the flow of urine from the bladder is a common phenomenon in women, particularly older women. Such inability to contain urine is termed "incontinence." Roughly half of elderly women are incontinent.

An incontinent women usually has an adequate reservoir (the bladder) for urine, but the biological "valve" is for one or another reason inadequate to prevent discharge of urine. The "valve" that normally performs this function is the urethra—the duct through which the bladder is normally emptied during urination—in conjunction with the muscle or sphincter that surrounds the urethra.

The most frequently encountered causes of incontinence in women may be classified as pathogenic, anatomical and neurological. Before incontinence in a particular women is treated, its cause must be ascertained. Not only is appropriate treatment for each kind of incontinence ineffective against other kinds of incontinence, but in some instances appropriate treatment for one type is counterproductive with respect to other types.

Incontinence that is pathogenic—caused by infection—is readily identified in ways that are outside the primary scope of my invention. (As will be seen, my invention is compatible with procedures for checking the possibilities of pathogenic incontinence.)

Anatomical and neurological incontinence, however, are readily contused by diagnosticians.

Distinguishing between them historically has been attempted by direct observations, and very recently has been accomplished by sophisticated instrumentation. Both of these systems will be described below. Unfortunately the direct observations are subject to several obstacles and inaccuracies, whereas the instrumentation is subject to such extremely high cost as to be accessible only to medical centers (as distinct from individual clinicians)—and even so is not free from certain inaccuracies and other disadvantages.

To understand the shortcomings of these methods it is necessary to understand the behavior and causes of anatomical and neurological incontinence. Both of these types appear in response to bodily stress, and particularly as reactions to a relatively abrupt increase in pressure within the abdomen.

(Traditionally the anatomical type of incontinence has been identified as "*genuine* stress incontinence" though both of these two types are in fact triggered by stress, and it may therefore be more accurate to describe both as, at least, "stress incontinence.")

A cough, sneeze or laugh is often the stimulus for such a pressure increase, but in more advanced stages of incontinence the patient may be unable to contain her urine even against pressure increases such as are incurred through light exercise: lifting, bending down, running, or even merely walking. Since these sorts of stress are basic to everyday living and use of the body, it will be apparent that advanced stress incontinence is virtually debilitating. Patients in which such conditions are untreated must resort to adult-size diapers or other cumbersome, relatively unsanitary, and potentially embarrassing appliances.

Stress-induced pressure increases, in normal women as well as women suffering from both types of stress incontinence, are transmitted to the bladder (though by different mechanisms), causing the pressure within the bladder to rise. In normal women, however, the pressure incurred by coughing, exercise, and so forth is exceeded by the pressure within the urethra.

When normal individuals are not urinating, the urethra is held closed by voluntarily controlled musculature (the sphincter surrounding the urethra), with the aid of surrounding anatomical structures. This musculature and other anatomical features produce a pressure within the urethra that exceeds any pressure ordinarily produced by stresses (pressures) transmitted to or arising in the bladder.

The higher pressure within the urethra stands off the liquid stored in the bladder, preventing the liquid from being discharged through the urethra and thereby out of the body.

There are primarily two ways in which this normal control system can fail: (1) the muscles and the structure that normally hold the urethra closed can become weak, and (2) the body can malfunction in such a way as to amplify the pressure increase within the bladder. In either of these abnormal situations, the pressure within the urethra is insufficient to stand off the pressure in the bladder—and urine is forced outward from the bladder through the patient's urethra.

The first of these two kinds of failure is due to anatomical weakness: the bladder opening at the top of the urethra, and the inner (or proximal, in medical terminology) end of the urethra has lost its support. This weakening probably occurs either as a result of childbirth or as part of the general deterioration of bodily structures with advancing age, or both. The inner end of the urethra, in any event, undergoes "prolapse"—it falls down or slips from its normal position.

The resulting phenomena may be viewed in a relatively mechanical way: a sudden increase in pressure within the abdomen (as with a cough) is transmitted to the bladder, and bladder pressure becomes greater than urethral pressure. Urine is then forced outwardly through the urethra.

This is known as "genuine stress incontinence." It can be treated surgically, but not by administration of medicines.

The second of the two kinds of failure enumerated above, the amplification of the stress-induced pressure increase, can occur in a woman whose urethral pressure is ample to withstand the abdominal pressure increase that is *directly* associated with a cough, sneeze, laugh, or even vigorous exercise. In this second kind of incontinence, however, the increased pressure within the bladder triggers nerve signals, and these nerve signals abnormally stimulate the bladder to contract. The contraction of the bladder in turn raises the pressure within the bladder very severely—to a level considerably greater than that produced directly by the stress.

The nerve signals triggered by the original pressure increase in the bladder may travel to the brain, causing return signals to the bladder along nerve paths normally used by the patient to squeeze the bladder and thereby help expel urine from the bladder. It is also possible that the nerve signals cause a more-localized chain reaction of spasms that eventually return to squeeze the bladder. Whatever the specific mechanism, this type of incontinence is characterized by a time delay of at least three to five seconds, and sometimes as long as fifteen to twenty seconds, between the originating stress and the responding contraction and discharge. In addition to the difference in timing, this type of incontinence also is usually characterized by a greater volume of discharge.

This type of stress incontinence is often called "bladder instability." It can be treated by administration of medicines, but not by surgery. In fact, attempts to correct it surgically often result in aggravating the condition.

(b) The "Stress Test"—A historically common method of determining which type of incontinence a woman has is the so-called "stress test" introduced by Doctors Bonney, Marshall and Reid. In the stress test the patient's bladder is filled with fluid (often a quarter of a liter of salt solution) and she is asked to cough. If fluid is discharged from her urethra immediately, the patient is diagnosed as suffering from "genuine stress incontinence" and requiring surgery, whereas if there is a delay the patient is diagnosed as having "bladder instability" and requiring medication. The test of course relies upon the difference in timing between the two kinds of reaction. Unfortunately this so-called "stress test" is flawed in several ways.

First, about half of incontinent women are continent when lying down. This fact results from the force of gravity on fluid in the bladder and on other bodily organs near the bladder. In a standing patient the proximal end of the urethra is essentially at the bottom of the pool of fluid in the bladder, and gravity adds substantially to the stress-induced pressure at the proximal end of the urethra. Furthermore, the weight of organs that are above the bladder tends to be applied to the bladder when the patient stands.

When the patient reclines, however, the rotation of the bladder and surrounding structures places the proximal end of the urethra much closer to the upper surface of the fluid in the bladder, or even above the upper surface, so that gravity makes no substantial addition to the stress-induced pressure at the proximal end of the urethra. At the same time there are fewer organs disposed to press upon the bladder when the patient reclines.

Hence the test must be conducted with the patient standing. Unfortunately, however, it is very undesirable to perform such a test with the patient standing. The standing patient will not generally be able to spread her legs sufficiently to allow the diagnostician a clear view of the distal (outer) end of the urethra. Consequently the diagnostician usually inserts her or his fingers within the patient's labia (the folds of flesh covering the vaginal outlet) to determine when that area is wetted by discharge of fluid. Under such conditions it is extremely difficult to accurately determine the timing of the discharge relative to the stress, especially considering that in some patients suffering from bladder instability the time delay is only three seconds.

Secondly, in a setting such a doctor's office the patient is often anxious. This often causes the voluntary sphincter of the urethra to go into involuntary spasm (that is, to squeeze the urethra shut), which obstructs the flow of fluid from the bladder. It has been shown that one-third or more of incontinent women may be unable to demonstrate incontinence under these circumstances. After leaving the doctor, however, the patient may again become incontinent.

This problem is aggravated by the fact that the patient must stand during the test, essentially confronting the doctor, with the doctor's fingers placed within the patient's labia. This confrontation accentuates the patient's realization that any fluid lost will wet the doctor's fingers, and such behavior of course contradicts all normal social schooling. As a result, in addition to the involuntary anxiety spasm discussed in the preceding paragraph, many patients may actually consciously squeeze the urethral sphincter more forcefully than they may normally squeeze during coughing, sneezing, exercising, etc.—thereby defeating the test.

Thirdly, many women have relatively large labia, which can act as a dam to discharge of fluid from the urethra. This effect makes it very difficult to determine whether fluid from the bladder is lost immediately or after a delay.

Fourthly, many women are obese, and the compound obstructions formed by rolls of flesh and folds of skin at the thighs of an obese patient similarly dam the fluid emerging from the urethra. The timing determination is accordingly impeded.

Fifthly, in any observation of biological phenomena there is a certain amount of imprecision. Diagnosticians may find that a discharge occurs with a seeming delay of one or two seconds, which does not correspond neatly to either category of stress incontinence. Similarly diagnosticians may find that some discharge occurs immediately after stress, and that an additional discharge "seems" to occur later. It must be realized that some women suffer from both types of incontinence, which would account for a dual discharge, but it is extremely difficult to determine reliably that a second discharge has occurred after the labia and the diagnostician's fingers are already wetted.

(c) Other Direct Observations—Partly as a result of the difficulties just described, diagnosticians usually perform other tests to gather additional information on the patient's anatomical condition. In particular, one common test—familiarly known as the "Q-tip test"—involves inserting a "Q-tip" cotton swab partway into the urethra, while the patient is lying on her back in the customary pelvic-examination position, and instructing the patient to bear down (as in defecation). In these circumstances the swab initially is generally horizontal, and deflects upward when the patient bears down.

In a normal patient the upward deflection does not exceed roughly thirty degrees. In the abnormal anatomical condition that gives rise to so-called "genuine stress incontinence," however, the upward deflection can approach ninety degrees. Since many diagnosticians are accustomed to including this test in their "work up," it is desirable to ensure that any new procedure proposed is compatible with—or, preferably, facilitates—some version of the "Q-tip test."

Similarly, it is generally routine to take a sample of urine directly from the patient's bladder. Such a sample is helpful in checking for pathogenic conditions, since it is less likely than an excreted sample to be contaminated by chance unsanitary conditions within or just outside the patient's labia. Consequently in any new procedure the obtaining of such a sample should be facilitated.

(d) Modern Instrumentation—The ambiguities in the now-classical "stress test" have led to introduction of electronic instrumentation for determining pressure relationships between the bladder and the proximal end of the urethra.

Such instrumentation generally consists of (1) a first pressure sensor that is inserted entirely through the urethra into the bladder, to sense the pressure within that organ; (2) a second pressure sensor that is inserted partway through the urethra, to sense the pressure along that duct, and (3) electronics and display devices for determining and recording those two pressures as they change with time, and in some instruments for also determining and recording certain relationships between those pressures.

The pressure sensors used may be of two different types. First, a pressure sensor may consist of (a) a small transducer, positionable within the bladder or urethra, that controls an electrical resistance or an electrical voltage source—together with (b) electrical leads for directing to the exterior of the body electrical signals related to the sensed pressure, and (c) a rod or the like for inserting the transducers and leads into position, and holding them in position, for measurement.

The other type of pressure sensor may consist of (a) a pair of tubes inserted into the bladder and urethra respectively, and (b) pressure-measurement devices attached to the ends of the tubes that are outside the body, to measure the pressure transmitted through the tubes while the tubes are held in position. With this type of sensor, the tubes are usually provided in the form of a single tube structure with parallel channels within it, and separate openings spaced along the tube near its proximal end.

In use of these instruments, the pressure sensors (of either type) are inserted together into the urethra while the patient reclines in the usual pelvic-examination position. One sensor is advanced approximately two to three inches forward of the other sensor, while the instrument operator observes the changing pressure readouts from the instrument. When the readout from the forward or proximal sensor decreases (indicating that the sensor has passed from the urethra into the bladder) but the readout from the rearward or distal sensor remains higher (indicating that this sensor has not yet reached the bladder), the insertion is stopped and data are taken.

In one very expensive unit, the instrument operator advances the sensor pair into the urethra and bladder, and then the apparatus (rather than the operator) automatically withdraws the catheter at a regular velocity, while measuring and recording the pressure relationships between bladder and urethra.

In other parts of the diagnosis the patient is instructed to cough, laugh, exercise, or otherwise incur abdominal stress, and the sensor measurements are recorded as they respond to the stress.

Instruments of this type are operationally preferable to the "stress test." The sensors can be emplaced while the patient is lying down and are relatively unintrusive, making insertion fairly easy.

Because, the apparatus is very sensitive and relies upon pressure measurements rather than actual discharge of urine, it appears from the literature that for some patients the entire test can be successfully (that is, accurately) conducted while the patient reclines.

Yet modern instrumentation for stress-incontinence diagnosis is unsatisfactory in at least four ways:

First, there remains a very large fraction of the population of incontinent patients whose incontinence is masked by the patients' lying down.

Secondly, the equipment is prohibitively expensive for use by individual clinicians. The cost for one operational device ranges roughly from $7,000 to $50,000, depending upon the degree of automaticity desired. Modern medical philosophy, however, for very good reasons favors acquiring as much information as possible in the doctor's office, rather than in the hospital or large-scale medical center.

Although this instrumentation has found an effective market among high-volume diagnostic laboratories such as those found in medical centers, even as evaluated by these facilities such an instrument is inordinately expensive.

Thirdly, its operation is surprisingly time-consuming, requiring generally an hour to an hour and a half for full diagnosis of each patient—though only a part of this time is occupied by the actual testing. This inordinate consumption of time is wearing on the patient, and also is expensive in terms of laboratory personnel.

Fourthly, many a patient (particularly among the elderly) finds it personally degrading or offensive to have her genital region connected to a machine. This is particularly true if a cost-conscious technician, having set up the test, goes off to tend to other business—leaving the patient to lie for an hour with wires trailing from her vulva to a box of electronics. Resulting psychological effects can disturb the measurement.

Finally, in a relatively small number of patients, the tube or rod used to advance the forward sensor into the bladder may irritate the opening of the urethra into the bladder, and this irritation may cause spurious indications from the instrumentation. In particular, such irritation may have a slight tendency to produce an emulation of bladder instability, or to suppress an already existing tendency toward bladder instability. On the other hand, such irritation may also have some very slight tendency to stimulate the urethral sphincter to close either more or less forcefully than it customarily does—thereby either suppressing or emulating the observable characteristics associated with genuine stress incontinence.

Although this last-mentioned set of problems is not a major drawback, it is of some interest in relation to my invention, as will be seen.

(e) Externally Stabilized Catheter—Doctors Sutherst and Brown of the University of Liverpool have described their studies of incontinence diagnosis making use of a two-channel catheter with a proximal end of one channel positioned within the urethra. 34 *Urologia Internationalis* 403 (1979), 52 *British Journal of Urology* 138 (1980), 53 *British Journal of Urology* 360 (1981).

In some of these studies the catheter was stabilized to the exterior of the patient's body to "prevent movement due to its weight and connections". The stabilization was accomplished by means of a "spring paper clip fixed to a flexible ring pessary . . . held between the patient's thighs".

Although these studies offered favorably high correlations between observed liquid discharge and other indications of "genuine stress incontinence," the experimental arrangements were in several ways marginal from the viewpoint of an individual clinician. The external appliance worn by the patient to stabilize the catheter would produce considerable patient discomfort if the patient were to bend, stretch, or even walk, since the urethral meatus in particular (which would be abraded by such activities) is very sensitive. Consequently in the studies described the patient could only be "tilted to the erect position on a motorised bed." Such an apparatus, of course, is far beyond the scope of equippage for the vast majority of individual clinicians.

In addition, the appliance would tend to fix the rearward end of the tube too securely to the patient's body, preventing effective incorporation of the "Q-tip test" into the diagnostic apparatus and method. As will be apparent, all of these limitations would very severely limit the feasibility of the published method for practical everyday clinical use.

(f) Appliances Used in Other Procedures—The foregoing discussions encompass prior approaches to diagnosis of stress incontinence. Certain prior-art devices used in other medical procedures, however, are related to my invention and bear mention here.

One of these devices is a catheter tube. Catheters are slender but strong tubes, usually flexible, used for innumerable purposes in medicine, and particularly in investigation of the urinary tract and virtually all other bodily cavities. They have been used in prior methods for incontinence diagnosis in three ways.

First, they are generally used to take urine samples from within the bladder as previously mentioned—principally for investigation of pathogenic incontinence, as distinguished from stress incontinence. Secondly, as previously mentioned they are used in some of the instruments described above to transmit bladder and urethral pressure to pressure gauges outside the patient's body. Thirdly, as previously mentioned, catheters are proposed in one known system for stress-incontinence diagnosis, involving stabilization of a catheter to the patient's thighs.

Catheters are made from a great variety of materials, but generally speaking the materials are selected and processed for *smoothness* and relative *stiffness* of the finished product—so that the catheters can be slid smoothly through the body openings or ducts of interest. Thus elastomeric catheters are generally manufactured with durometer (an industrial measure of hardness) between seventy and ninety.

Also as a general rule catheters are long enough to pass into the body organ or vessel of interest, and if a catheter is longer than necessary to satisfy this condition, the excess length is of no consequence.

Another relevant device is a bougie (usually pronounced "BOO-zhee"). It is a generally cylindrical instrument or article, sometimes tapered, for insertion into a tubular passage of the body. Bougies have a variety of purposes, not previously including diagnosis of incontinence. Prior-art bougies have been *solid*, in the sense that they have not had apertures formed in them.

One kind of bougie is known in medicine as a "lamineria." It is a small piece of extremely hygroscopic (water absorbent) material—essentially a super-sponge. One kind of lamineria is inserted into the cervix or mouth of a woman's uterus in preparation for childbirth, to remove water from the tissue there. Originally a lamineria was made from a particular species of seaweed, but more recently an artificially made polyvinyl-alcohol sponge has been used. In cervical dilators the polyvinyl-alcohol sponge is generally impregnated with synthetic magnesium sulfate to enhance, and particularly to accelerate, the absorption and expansion.

The object of such a lamineria is to remove naturally occurring moisture. Incidentally to that object the lamineria swells very substantially as it takes up water. Such devices have not been used in diagnosing incontinence.

BRIEF SUMMARY OF THE INVENTION

1. Diagnostic Apparatus

My invention provides extremely inexpensive apparatus for use in diagnosis of incontinence in a woman by investigating movement of liquid from her bladder into her urethra. My invention also provides an extremely simple, quick method for diagnosing such incontinence, using such apparatus.

The apparatus includes a tube that has two open ends, and that is narrow enough and long enough to extend entirely through a woman's urethra and into her bladder.

The apparatus also includes some means for anchoring the tube within and relative to the urethra. In particular these "anchoring means," as they may be called, are adapted for anchoring the tube inside the urethra with a first end of the tube slightly withdrawn from the bladder, while the other end of the tube extends outwardly through the urethra and out of the woman's body.

The tube preferably is short enough to extend only a short distance out of the patient's body when thus positioned, so that the patient can conveniently and comfortably walk about while the tube is emplaced. Furthermore, it is important to position the anchoring means themselves within the woman's body, to avoid the limitations of the externally stabilized catheter previously discussed.

This apparatus thus provides reliable and rapid liquid communication between the inside of the urethra, at a point just below its opening from the bladder, and the space just outside the patient's body.

Liquid that is released from the bladder through the inner end of the urethra reaches the first end of the tube. Once liquid has reached that point it is conducted substantially immediately, via the interior of the tube, out of the woman's body and into view by the diagnostician.

In this way the specially positioned and anchored tube *bypasses* the sphincter of the urethra—thereby rendering the examination immune to the two kinds of psychological effects discussed earlier—and the tube also bypasses any obstructions formed by the labia or the flesh of the thighs, thereby rendering the examination independent of such structures that in the prior art have created observational problems.

In practice, the diagnostician using this system can very readily determine the time relationships between a cough or other stress and the discharge of urine from the bladder into the *upper* part of the urethra.

Preferably the anchoring means and the tube are readily removed from the patient's urethra, after the test, by modest tension applied to the outer end of the tube.

I prefer to provide the "anchoring means" in the form of two separate features—and with the aid of certain material characteristics of the tube itself. One of these features is an anchoring element that is adapted to surround the tube, and to slide along the outside of the tube. Preferably the anchoring element is formed with a hole through it, to permit the tube to be inserted into and through the anchoring element. This anchoring element is preferably adapted for enlargement radially, relative to the tube, against the interior of the urethra.

A particularly convenient way of providing such an enlargeable anchoring element is to use a material that absorbs liquid and that thereby expands at least severalfold. The same materials used to make lamineriae—hygroscopic materials such as synthetic magnesium sulfate—may be used to make liquid-absorbing anchoring elements for use as part of my invention.

One beneficial aspect of using this kind of material for an anchoring element is that the material (and hence the element) is very soft when expanded. This is important because the interior of the urethra is extremely delicate and sensitive.

The other feature which I prefer to use in providing the "anchoring means" is an enlargement in the exterior wall of the tube, near the forward (proximal) end of the tube. This enlargement is preferably small, and preferably gently rounded at its forward and rearward (proximal and distal) ends.

In addition, as previously mentioned, I prefer to provide a tube that itself has material characteristics which aid in the anchoring. Specifically, I prefer to use a tube that is of relatively soft and flexible elastomer.

Such a tube distinctly resists falling out of the urethra under the influence of gravity, since it conforms somewhat to surface irregularities of the urethral wall and also because its own surface is almost "tacky." As will be recalled, such a specification for catheter tubes runs contrary to the conventional teachings of smoothness and stiffness for such tubes. In fact, the tube of my invention is generally too limp, by itself, to be pushed into place within the urethra; insertion of the tube therefore usually requires preinsertion of a stiffening element into the catheter. This same stiffening element may be used in a version of the "Q-tip test," as will be detailed later.

My invention also preferably includes some means for facilitating introduction of the tube and of the anchoring means into the urethra. These means, which may be called "facilitating means," advantageously include a guide element that is adapted to fit within and to spread the outer opening or "meatus" of the urethra. Such a guide element should have formed in it a passageway extending entirely through the guide element, from a first orifice at one end of the passageway to a second orifice at another end of the passageway. The passageway in the guide element should be large enough to accommodate the tube.

When the guide element is fitted within the urethral meatus, in position to spread the meatus, the passageway is very generally aligned with the urethra. Consequently the first end of the tube may be very readily inserted through the guide element into the urethra.

The passageway in the guide element advantageously is also large enough to simultaneously accommodate the anchoring element during insertion of the anchoring element into the urethra. The anchoring element accordingly may be inserted through the guide element into the urethra.

The facilitating means advantageously also include a handle affixed to the guide element. The handle should be adapted to be grasped by the patient while the guide element is fitted within the patient's meatus. In this way the patient may aid in stabilizing the guide element to aid the diagnostician.

In some cases the patient may simultaneously aid the diagnostician in establishing access to the meatus from outside her body. This can be very helpful in the case of a patient who has very thick or extensive labia, or whose thighs are obese and tend to impede the diagnostician's access to the vulval area. By use of the handle on the guide element the patient may hold the guide element in position and at the same time aid in holding the labia or the flesh of the thighs, or both, out of the diagnostician's way.

Not only does this feature of my invention aid the work of the diagnostician, but it also helps to minimize the "poking and prying" that must be done by the diagnostician. It thereby can help to minimize the patient's embarrassment and other psychological discomfort.

Preferably the guide element has an outside surface that is tapered from a narrower portion generally adjacent to the first orifice mentioned above, to a wider portion generally adjacent to the second orifice. The guide element thus is readily inserted, with its narrower portion leading, into the meatus.

Advantageously the inside surface of the passageway within the guide element also has a narrow portion generally adjacent to the first orifice, and a wider portion generally adjacent to the second orifice. This configuration increases the ease with which the tube can be inserted into the wider portion of the passageway, and thence through the narrower portion of the passageway past the meatus into the urethra.

When the passageway within the guide element is large enough to accommodate the anchoring element, the anchoring element too may be readily inserted into the wider portion of the passageway, and thence through the narrower portion of the passageway into the urethra. The anchoring element may then surround and slide along the outside of the tube, but within the passageway in the guide element.

When an enlargeable anchoring element is so positioned on the tube and is being inserted into the guide element, and is within the guide element, the anchoring element preferably is not yet enlarged. It is not enlarged until it has been emplaced—or just as it is being emplaced—in the urethra.

After the anchoring element has been inserted through the guide element so that at least a substantial part of the anchoring element is in direct contact with the urethra, the guide element is made to enlarge radially against the interior of the urethra. The tube is thereby anchored within and relative to the urethra, with the first end of the tube slightly withdrawn from the bladder. (Anchoring is preferably aided by the previously mentioned enlargement near the proximal end of the tube.) The procedure for placing the tube in this position, preparatory to anchoring it, will be described shortly.

My invention also contemplates simple and inexpensive means by which a diagnostician can monitor the pressure within the bladder while inducing the patient to undergo stress and while observing the timing of the discharge in relation to the onset of the stress. The reason for this provision is that, as mentioned earlier, biological observations are often complicated by a failure of observed phenomena to fall straightforwardly into theoretical categories.

Additional information is almost always helpful in resolving the resulting ambiguities. For example, when the patient goes through the motions of coughing, the externally observable "cough" may not coincide precisely with the peaking of the directly produced pressure pulse within the abdomen—and thus within the bladder.

When urine discharge occurs just two or three seconds after the apparent "cough," a pressure measurement may reveal that the bladder pressure actually underwent an abrupt step shortly after the "cough" and therefore in close synchronism with the discharge. The diagnosis therefore could be more confidently one of genuine stress incontinence. On the other hand, pressure measurement may reveal that the bladder-pressure step occurred *before* the patient appeared to cough, and therefore that the actual delay was perhaps four or five seconds. In such a case too a more confident diagnosis could be made, but it would be of bladder instability.

One setup for monitoring pressure inside the bladder involves a long, very slender hypodermic needle inserted through the patient's abdomen and into her bladder, and a pressure monitor attached to the distal (outer) end of the needle. Although this arrangement is clinically unobjectionable and quite painless—particularly with a local anesthetic—many patients find such an arrangement utterly petrifying. The resulting psychological effects may well disturb the measurement as well as the patient's peace of mind.

Accordingly, for patients who find that arrangement undesirable, my invention advantageously includes a second tube, also long enough to extend entirely through the urethra and into the bladder. This second tube, unlike the first, is particularly adapted to be held in a position within the urethra with one end extending into the bladder and the other end extending out of the body, while the first-mentioned tube is anchored with its first end slightly *withdrawn from the bladder*. With this apparatus, pressure in the bladder may be measured through the second tube contemporaneously with observation of stress onset, and of resulting liquid discharge from the urethra through the first tube.

In purest clinical principle, setting aside psychological considerations for the moment, this second tube may not be as desirable as the hypodermic mentioned earlier, since the second tube may slightly irritate the proximal end of the urethra, at the point where the urethra opens into the bladder. Such irritation may have some very slight tendency to modify the magnitude or timing of stress-induced liquid discharge, and thus to generate diagnostic artifacts.

Such interference, however, should be no more serious than that associated with the forward pressure sensor used in the prior-art electronic instrumentation discussed above. To the extent that such a risk is acceptable in a $50,000 piece of equipment, it should be acceptable in apparatus that costs $50 or $20 or even less. No diagnostic apparatus or procedure in this field can be absolute.

On balance, if a particular patient's diagnosis using the single tube is ambiguous and the patient would be significantly upset by use of a hypodermic, the dual-tube configuration is likely to be useful in resolving the diagnostic ambiguity. Alternatively, the dual-tube configuration may be used routinely for initial tests. If the diagnostician detects any erraticism in the results that may suggest irritation of the proximal end of the urethra, another session may be scheduled for diagnosis using the *single*-tube configuration.

Regardless of the order of events, the very slight drawback of the dual-tube configuration is thus readily overcome by intelligent use of the apparatus and method. A medical technician (as well as a nurse or physician) who carefully reviews the foregoing cautions and the detailed discussion which follows will be readily enabled to practice my invention with a very high diagnostic accuracy.

2. Diagnostic Method

As suggested in the foregoing description of apparatus provided by my invention, the invention also includes a procedure or method for diagnosing stress incontinence in a woman, by investigating movement of liquid from her bladder to her urethra. The procedure involves these basic steps:

positioning a tube partly within the urethra, with the proximal (inner) end of the tube at least slightly withdrawn from the bladder, and the distal (outer) end of the tube extending outwardly through the urethra to the outside of the woman's body;

while the tube is so disposed, causing the woman to undergo stress of a type which induces such incontinence; and observing the timing of discharge of the liquid relative to incidence of the stress.

The method preferably also comprises certain other steps, which aid in ease or reliability of the observation, or in minimizing the patient's distress:

anchoring the tube in the position described; and measuring pressure within the bladder, and observing the timing of changes in bladder pressure relative to liquid discharge and stress onset.

Preferably the positioning step includes inserting a stiff conical sheath into the patient's urethral meatus, and inserting the tube through the sheath into the urethra. In addition, the anchoring step preferably includes two substeps: sliding an anchoring element around and along the tube, from the distal end of the tube into the urethra, and then causing the anchoring element to enlarge radially, relative to the tube, against the interior of the urethra.

The procedural features described in the preceding paragraph are particularly advantageous if, in addition, the "sliding" substep includes sliding the anchoring element along the tube and *through the conical sheath* into the urethra. This sliding substep should be performed while the tube is inserted through the sheath into the urethra. This particular innovation makes it possible to emplace the anchoring element at its functioning location easily and quickly, without abrading the sensitive urethral tissue, and without running the risk of premature enlargement of the anchoring element by exposure to moisture in the meatus.

All of the foregoing operational principles and advantages of the present invention will be more fully appreciated upon consideration of the following detailed description, with reference to the appended drawings, of which:

BRIEF DESCRIPTION OF THE DRAWINGS

FIGS. 1 through 10 illustrate preferred embodiments of my diagnostic apparatus, and FIGS. 11 through 22 illustrate progressive stages in a preferred embodiment of my diagnostic method.

FIG. 1 is a generally isometric view of a tube for use as part of the diagnostic apparatus of my invention, an in practice of the diagnostic method of my invention.

FIG. 2 is a similar isometric view of a bougie for use with the FIG. 1 tube. In FIG. 2 the bougie is shown in its dry condition—that is to say, unexpanded.

FIG. 3 is a similar isometric view of the FIG. 2 bougie in place on the distal end of the FIG. 1 tube. In FIG. 3 the bougie is shown in its wet condition, enlarged.

FIG. 4 is a similar isometric view of a "facilitating means" for use in facilitating insertion of the FIG. 1 tube and FIG. 3 bougie into a woman's urethral meatus.

The facilitating means include a guide element, sometimes called a conical sheath, with an integral handle.

FIG. 5 is a cross-sectional view of the FIG. 4 facilitating means (guide element or conical sheath, and handle), taken along the line 5—5 of FIG. 4, and with the end of the handle omitted to constrain the size of the drawing.

FIG. 6 is a side elevation of a guide rod for use in positioning the facilitating means of FIGS. 4 and 5.

FIG. 7 is a similar elevation of a stiffener for use with the FIG. 1 tube, in inserting the tube into the urethra and also in performing an adaptation of the conventional "Q tip test."

FIG. 8 is a generally isometric view of the FIG. 5 facilitating means as used with the FIG. 6 guide rod.

FIG. 9 is a similar isometric view of the FIG. 1 tube as used with the FIG. 2 (unexpanded) bougie and the FIG. 5 facilitating means. In FIG. 9 the bougie is simply placed over the distal end of the tube.

FIG. 10 is a similar isometric view of the same articles as in FIG. 9, but with the bougie partially inserted through the facilitating means.

FIG. 11 is a somewhat schematic drawing showing a supine woman's pelvic region in cross-sectional elevation, and showing in external elevation a guide rod inserted into the urethra in preparation for positioning of the facilitating means.

FIG. 12 is a similar schematic view showing the sheath portion of the facilitating means inserted along the guide rod into the urethral meatus.

FIG. 13 is a similar view showing the rod removed.

FIG. 14 is a similar view showing the tube inserted through the sheath and partway through the urethra.

FIG. 15 is a similar view showing the tube inserted entirely through the urethra into the bladder.

FIG. 16 is a similar view showing the tube slightly withdrawn from the bladder (as in FIG. 14), and the bougie now inserted partway through the conical sheath and into the urethra.

FIG. 17 is a similar view illustrating the removal of the conical sheath and simultaneous enlargement of the bougie.

FIG. 18 is a similar view showing the bougie enlarged within the urethra.

FIG. 19 is a similar view showing the stiffener inserted into the tube.

FIG. 20 is a similar view, but with the stiffener removed and the patient standing.

FIG. 21 is a similar view, but with the patient again supine and the tube partially withdrawn for removal of the bougie.

FIG. 22 is a similar view, but with the bougie removed from the tube and the tube reinserted into the bladder.

FIG. 23 is a generally isometric view, similar to FIG. 1, of a two-channel tube that is another preferred embodiment of my invention.

FIG. 24 is an end elevation of the FIG. 23 tube.

FIG. 25 is a schematic drawing similar to FIG. 18, but showing in use the embodiments of FIGS. 23 and 24 rather than the FIG. 1 embodiment.

DETAILED DESCRIPTION OF PREFERRED EMBODIMENTS

As shown in FIG. 1, most of the tube 11 is a right-circular cylinder 12, but near the forward (proximal) end 13 of the tube 11 there is preferably formed a bulb-like enlargement 14. This enlargement 14 helps to anchor the tube within the urethra, and also prevents the bougie from coming off the forward end of the tube inside the urethra—in the unlikely event that the expanded bougie does not grip the tube wall 12 firmly enough.

The forward end 13 of the tube 11 is advantageously cut off or otherwise formed at roughly a forty-five degree angle, and the resulting edges smoothed to avoid cutting or abrading the patient's urethra. The rearward (distal) end 17 of the tube 11 may be simply cut off square, and the edges smoothed.

It is helpful to the diagnostician to provide distance indicia 15 and corresponding calibration indicia (numerals) 16, as measured from the forward end 13 of the tube The tube 11 is advantageously of material known commercially as "Silastic," and for suitable flexibility and tackiness it is preferably relatively soft—as, for example, of durometer between roughly forty-five and fifty-five.

For reasons previously explained the tube is preferably short enough to protrude only two to four inches from the patient's body; thus it may be roughly 5½ inches long, and approximately "twelve French" (using standard medical-appliance terminology) or 0.134 inch in outside diameter The inside diameter is preferably about 0.079 inch.

The enlargement 14 advantageously has a maximum outside diameter of about 0.185 inch, so that the enlargement extends roughly 0.025 inch radially outward from the cylindrical surface 12. The enlargement 14 advantageously consists of a surface that is a figure of revolution about the central axis of the cylindrical surface 12. The enlargement surface 14 advantageously has a radius, in the plane of the central axis, of about 0.825 inch; the center of curvature is preferably about 0.45 inch rearward of the forwardmost tip of the forward end 13 of the tube. The center of curvature is preferably placed about 0.733 inch (or about five and a half tube diameters) beyond the central axis of the cylindrical surface 12.

FIG. 2 shows generally the bougie 21 that is provided for use with the tube 11. For definiteness the bougie 21 is illustrated as an annular cylinder, with internal cylindrical surface 22 and regularly terminated ends 23 and 24. In practice, however, the bougie 21 is slightly compressible and somewhat irregular in shape (particularly after it has been used one or more times) because of the properties of the material from which it is made. That material is advantageously a polyvinyl-alcohol sponge, which expands when wetted and contracts when dried.

The sponge can be impregnated with magnesium sulfate or some other highly hygroscopic material, as is done in making unperforated polyvinyl-alcohol sponges for use as cervical dilators. Such material is available commercially in the desired configuration, to order, from the Hirol Company of Fort Lauderdale, Fla., or the Cabot Medical Corporation of Langhorn, Pa. It appears fairly likely, however, that the impregnate (magnesium sulfate or the like) can be omitted, and that a suitable bougie can be made relying on the porosity of the sponge alone.

To prevent transfer of pathogens between patients, the bougie and catheter should be treated as disposable—that is to say, each should be destroyed after just one use.

The internal surface 22 of the dry, unexpanded bougie 21 has approximately the same inside diameter as the outside diameter of the cylindrical surface 12 of the tube 11. The dry bougie therefore can be slid onto the tube 11 from the rearward end 17, the slight compressibility of the bougie accommodating any initial interference fit.

FIG. 3 shows the enlarged bougie 21' after it has been slid onto the cylindrical surface 12 of the tube and wetted. (In this view the forward end of the tube 11 has been omitted by terminating the drawing at 18.) When wetted the bougie 21' has some tendency to expand inwardly against the exterior wall 21 of the tube, as well as outwardly. Consequently the bougie 21' grips the cylindrical surface 12 more firmly after being wetted than before.

FIGS. 4 and 5 illustrate the facilitating means. As can be seen they consist of a sheath 31 with an integrally attached handle 41. The outside of the sheath should have a relatively long portion 32 that is tapered, narrower at its forward end, to ease insertion of the forward end into a patient's urethra. By virtue of this tapered portion 32 the sheath 31 may be described as conical.

The outside of the sheath 31 advantageously also has a generally cylindrical short forward tip 33 and a generally cylindrical rearward body 34. If desired the rearward end 35 of the cylindrical body 34 may be beveled as shown.

Most of the inside surface 36 of the sheath is advantageously cylindrical, but the rearward end may be outwardly flared as at 38, to facilitate insertion of the tube and particularly of the dry bougie 21 into the sheath. The cylindrical inside surface 36 of the sheath 31 is larger than the maximum outside diameter of the tube enlargement 14, and is generally the same size as the outside diameter of the bougie 21 when the bougie is dry. Any slight tendency to an interference fit is readily overcome by compression of the bougie 21.

A shallow cylindrical hole 37 is advantageously provided in the cylindrical outside wall 34 for attachment of a handle 41. This cylindrical hole 37 preferably has its axis generally perpendicular to the central axis of the tapered surfaces 32, 35 and 38 and the cylindrical surfaces 33, 34 and 36. The handle 41 is generally cylindrical, but may have a knurled section 42 to afford a better grip, a beveled edge 43 at the remote end, and other convenience features as desired. For convenience of illustration in FIG. 5 the handle is shown cut off at 44.

I prefer to make the sheath 31 about 1.4 inch long overall—about 0.6 inch of this length being allocated to the tapered portion 32. About 0.1 inch is allocated to the forward cylindrical tip 33, about 0.6 inch to the rearward cylindrical body portion 34, and about 0.1 inch to the rearward beveled section 35. The outside diameter of the forward tip 33 is about 0.375 inch, and that of the rearward cylindrical body portion 34 is about 0.62 inch. The inside diameter of the cylindrical barrel 36 is about 0.31 inch.

In my preferred embodiment the handle 41 is about six inches long, including a 3½-inch section that is knurled. One end of the cylindrical surface 42 of the handle 41 is cemented (or, if metal parts are used, can be welded or brazed) into the shallow cylindrical hole 37 in the body 34 of the sheath 31.

As shown in FIG. 6, the guide rod 51 is a simple cylindrical shape 52 with a rounded end 53 and a short knurled handle 54. The cylindrical portion 52 should be about four inches long, and 0.3 inch in diameter, for easy sliding fit within the cylindrical barrel 36 of the sheath 31.

FIG. 7 shows that the stiffener 56 is a very slender rod 57 with a stop bulb 58 or other suitable enlargement 58 formed at one end. The rod 57 should have outside diameter selected to fit readily inside the tube 11 (FIG. 1)—and the stop bulb 58 should have outside diameter selected so that it will *not* fit inside the tube 11. The stop bulb 58 prevents the stiffener 56 from sliding entirely into the tube 11 (and thus out of reach) when the tube is inserted into the patient. The stiffener may be about 5½ inches long.

FIG. 8 shows the facilitating means 30 and guide rod 51 assembled as for the beginning of my diagnostic method. The facilitating-means sheath 31 is free to slide along the cylindrical part 52 of the guide rod 51.

FIG. 9 shows the tube 11 and the dry bougie 21 assembled for insertion into a patient's urethra. The forward end 23 of the bougie 21 has been slid over the rearward end 17 of the cylindrical surface 12 of the tube, and thence along the cylindrical surface 12 a short additional distance—so that the rearward end 24 of the bougie has also passed over the rearward end 17 of the tube 11, as shown. The stiffener 56 has been inserted into the tube 11 from the rearward end 17 of the tube—fully inserted except for, of course, the stop bulb 58. The drawing also shows the forward end of the tube 11 inserted through the sheath 31 of the facilitating means 30, which is my preferred way of inserting the tube into the urethra.

FIG. 10 shows the still-dry bougie 21 advanced along the tube 11 and within the sheath 31 of the facilitating means, so that the forward end 23 of the bougie 21 is protruding from the forward tip 33 of the sheath 31. As suggested in the sketch, in passing through the barrel of the sheath 31 the bougie 21 may undergo some radial compression, and to some extent the bougie may recover radially after it has reemerged from the forward tip 33 of the sheath 31.

The relative positions of the tube 11, bougie 21 and sheath 31 in FIG. 10 are generally those used immediately before expansion of the bougie within the urethra, to anchor the tube 11 within and relative to the urethra.

In FIGS. 11 through 22 the patient's abdomen 61, urethra 64, bladder 65, vagina 62 and uterine opening 63 are shown schematically in cross-section. The abdomen 61, vagina 62 and uterus 63 are illustrated only for purposes of orientation. The two ends of the urethra 64 are the outer (distal) "meatus" 65—the opening to the outside of the patient's body—and the inner (proximal) "vesical neck" 66—the opening to the interior of the bladder 65. To avoid unduly complicating the drawings the patient's labia are not illustrated, but it will be understood that they extend rightwardly in FIGS. 11 through 19, and 21 and 22, and downwardly in FIG. 20, from the meatus 65.

I normally begin my diagnostic procedure by preassembling the facilitating means 30 onto the guide rod 51 as in FIG. 8, and preassembling the bougie 21 onto the tube 11 as in FIG. 9. I also usually preinsert the stiffener 56 into the rearward end 17 of the tube 11, so that only the top bulb 58 protrudes.

Then (or at the same time) I ask the patient to recline in the usual pelvic-examination position—which is to say, lying supine with her legs apart—and I insert a Sims speculum into the vagina. I also ask the patient to spread her labia for greater exposure, and in particular to aid me in locating the meatus 65. When the patient's urethral meatus 65 is accessible I gently insert the tip 53 of the guide rod 51 into the meatus 65, to the position illustrated in FIG. 11.

The rounded tip 53 of the guide rod 51 enters the meatus without discomfort, in the sense of physiological trauma, to the patient—although there is of course an unaccustomed sensation. The same may be said of all the remaining stages of my diagnostic method.

Next I advance the facilitating means 30 along the guide rod 51 so that the forward tip 33 (FIGS. 4 and 5), and then the tapered section 32, also enter the meatus 65. Because of the very small annular thickness of the tip 33, and the very gradual taper of the tapered section 32, this insertion too produces little or no discomfort (in the sense already explained) to the patient. Also aiding in the avoidance of discomfort is the close alignment between the already-inserted guide rod and the sheath 31 of the facilitating means 30.

Next I ask the patient to grasp the handle 41 (FIGS. 4 and 5) of the facilitating means 30, and to hold the sheath 31 firmly in place within the meatus 65 while continuing to hold her labia apart. The patient usually finds it relatively easy to hold the labium on one side or the other with, for example, the outside of her thumb 68a (still with reference to FIG. 12) on one hand, while gripping the handle between the other side of that thumb 68a and the fingers 68 of the same hand.

I then remove the guide rod 51 and set it aside, leaving the facilitating means 30 inserted into the meatus 65 and held by the patient as shown in FIG. 13.

The next step is to insert the forward end 13 of the tube 11 through the sheath 31 of the facilitating means and into the urethra 64. Usually, as mentioned earlier, the bougie 21 has been preassembled onto the rearward end of the tube 11 (as shown in FIG. 9), and the stiffener 56 has been preinserted into the tube 11. If not, these preliminaries can be performed immediately before inserting the tube into the sheath 31.

In either event, the sheath 31 is stabilized within the meatus 65 by the patient herself, and I am able to insert the forward end 13 of the tube 11 into the position shown in FIG. 14—and then beyond that position, so that the forward end 13 of the tube passes through the vesical neck 66 into the bladder 65. An experienced diagnostician can estimate this condition from the markings 15, 16 on the tube wall 12 and the observed body size of the patient. As will be seen, however, if the tube is not inserted far enough the error creates no problem.

Here again, there is no discomfort to the patient, since the forward end 13 of the tube does not touch the relatively more sensitive meatus. Of nearly equal significance, there has been very little opportunity for contaminating contact between the forward (fluid-gathering) end 13 of the tube and the outer portions 65 of the patient's urethra.

When the forward end 13 of the tube is in the bladder 65 there is direct liquid communication between the inside of the bladder 65 and the outside of the patient's body. Therefore by removing the stiffener 56 I can verify that the forward end of the tube is in the bladder: a prompt and continuous liquid discharge should result. If not, the stiffener 56 can be reinserted, the tube advanced further through the urethra, and the stiffener again removed.

Once the forward end of the tube is in the bladder, I stop the liquid discharge by attaching a conventional stopcock (not illustrated) or some other closure means (such as a plastic tube with a tubing clamp) to the rearward end 17 of the tube. I then take an essentially uncontaminated sample of the patient's urine 67. A few cubic centimeters of urine is sufficient for analysis and culture. At this time I also take the opportunity to measure the functional length of the urethra, using the indicia 15 and calibration marks 16 on the tube 11.

Thereafter I generally fill the bladder, still using the tube in its FIG. 15 position, and attaching a volumetric syringe by means of the previously mentioned connections to the rearward end 17 of the tube. If desired to standardize the amount of liquid in the bladder 65, I can first drain all the urine 67 from the bladder, and then add a standard volume—generally about 250 cc—of saline solution.

When the appropriate amount of liquid is within the bladder 65, I can measure the pressure within the bladder by holding the syringe vertically and observing the height of the liquid in the syringe. Next I disconnect the liquid supply, and I observe the flow of liquid outwardly from the bladder through the tube while I withdraw the tube—by pulling gently on the rearward end. I continue to withdraw the tube until the liquid flow stops.

I know when the flow stops that the tube is once again in a position such as shown in FIG. 14, and particularly that the forward end 13 of the tube is just withdrawn through the vesical neck 66. In other words, the forward end 13 of the tube is just withdrawn from within the bladder 65.

It is in this position that the tube is to be anchored. To accomplish this I slide the bougie 21 forward from the position shown in FIG. 14 (and FIG. 9) through the sheath 31 so that the bougie is protruding slightly from the forward tip 33 (FIGS. 4 and 5) of the sheath. In other words, I move the bougie forward to the position shown in FIG. 16 (and FIG. 10).

Next I ask the patient to release the handle 41 of the facilitating means 30, which I grasp myself. Then I apply a small amount of water to the rearward end 24 (FIGS. 2 and 9) of the bougie, and essentially at the same time I draw the sheath 31 outwardly along the cylindrical portion 12 of the tube. The water may be applied through a small nozzle 72 of a laboratory "squeeze bottle" 71—the nozzle 72 being pointed into the outward or rearward end of the sheath 31—while the facilitating means 30 are pulled outwardly relative to the tube.

As will be apparent, the diagnostician may desire to develop some dexterity in this three-part motion, or the diagnostician may arrange for an assistant to apply the water so that two hands are fully available to hold the tube 12 and the sheath 31 respectively.

It will also be apparent that a "deluxe" version of the apparatus may be provided which includes a special (but inexpensive) hand tool for drawing the sheath outwardly along the tube while applying water to the rear of the bougie. Such a tool would be particularly formed to grip both the tube and the sheath simultaneously, and its moving parts would be simply arranged to afford the diagnostician continuous fine control of the extraction of the sheath along the tube—while expelling water onto the rearward end of the bougie.

The result of this maneuver, however conducted, is to expand the bougie, as shown at 21' in FIG. 18, against the inside of the urethra—just within the meatus 65—thereby anchoring the tube in the position shown in FIG. 18. By virtue of this accomplishment the remainder of the diagnosis is now rendered extremely straightforward, easy, and reliable, as will now be shown.

Once the bougie is anchored I prefer to reinsert the rod portion 57 of the stiffener into the tube 11 as shown in FIG. 19, and to ask the patient to "valsalva" or bear down as hard as she can. The stiffened tube 11 deflects upwardly as indicated by the arrows 59 in FIG. 19, the amount of deflection depending upon the loss of abdominal support for the urethra as previously mentioned.

Next I remove the stiffener, and ask the patient to stand. The patient's body and my diagnostic apparatus are then of course reoriented as shown in FIG. 20. The patient is asked to cough or to perform stressful maneuvers—from simply walking around the room to bending and lifting. Patients with "genuine stress incontinence" promptly lose a spurt of liquid; patients with "bladder instability" lose liquid after a short delay, and tend to lose a much larger quantity. In either case, the timing of the discharge is entirely clear since the discharge occurs from the end of the tube 11, bypassing the urethral sphincter, labia, and thighs.

When these observations have been completed, the patient again reclines, and I gently pull the tube 11 outwardly just far enough to bring the enlarged bougie 21' out of the meatus as shown in FIG. 21. Since the bougie 21' is very soft in its expanded condition, pulling it outwardly through the meatus does not cause the patient discomfort. I then slide the bougie the rest of the way off the end of the tube 11.

(In principle the bougie could fail to grip the cylindrical surface 12 with sufficient force to overcome the engagement of the bougie with the meatus, and the bougie accordingly could remain inside the meatus during the outward motion of the cylindrical part 12 of the tube 11. This has never occurred in my testing of the apparatus. If it did, however, the bougie would almost surely be removed by withdrawing the tube 11 from the meatus completely, since the enlargement 14 near the forward end of the tube 11 would engage the inside of the bougie 21' with greater force than the cylindrical surface 12.)

Next I reinsert the tube so that its forward end 13 is again within the bladder as shown in FIG. 22, drain the residual liquid through the tube, and finally remove the tube entirely. As a variant of the procedure, the tube can be withdrawn at the time the bougie is removed, and the patient asked to void; the tube or a conventional catheter can then be reinserted into the bladder to remove the urinary residual.

As seen in FIGS. 23 and 24, the dual-tube embodiment of my invention preferably employs a unitary tube structure 111 with a generally circular-cylindrical outside surface 112, but with an inner dividing wall 191 that segments the tube into two lumens or channels 192 and 193. One of the channels may be larger than the other, as shown.

One channel 192 is plugged at the end 113 of the tube that will be advanced forwardly—that is to say, at the proximal end (the right end of the illustration as drawn). Medical-grade silicon is suitable in plugging the channel. A lateral hole 194 is provided in the outside wall or surface 112 of the tube, communicating with this same channel 192.

The unplugged segment of this particular channel 192 (the portion between the lateral hole 194 and the rearward end 117 of the tube) will conduct liquid outside the patient's body, from the proximal end of the urethra. In other words, this channel 192 will perform the same function as the tube 11 in the previously discussed embodiment of my invention. Consequently the channel 192 may be called the "intraurethral discharge" channel. The outer surface 112 may be provided with an enlargement 114, just rearward (distal) from the lateral hole 194, for the same purposes as the enlargement 14 in the single-channel tube discussed previously.

The other channel 193 is not plugged, and has no lateral hole. This channel 193 will transmit pressure from within the patient's bladder to a pressure gauge outside the patient's body, and consequently may be called the "intravesical pressure" channel. It will be apparent that outside the patient's body attachments to the two channels 192 and 193 must be made in a slightly more elaborate fashion than to a single-channel tube. For example, fittings may be provided which are adapted for insertion into the distal ends of the two channels respectively, and which in turn are adapted for connection to individual tubes, or to a pressure gauge, a stopcock, and so on.

The way in which the two channels can perform their respective functions is generally illustrated in FIG. 25, which shows the same stage of the procedure for the dual-channel tube as FIG. 20 shows for the single-channel tube.

All of the procedures described in connection with the embodiment of FIGS. 1 through 22 are essentially the same when using the embodiment of FIGS. 23 through 25, except that (1) of course the diagnostician monitors the bladder pressure while observing the liquid discharge, and (2) if desired, a stopcock or other closure may be preattached to the intraurethral-discharge channel (the channel that has the more rearward orifice), while the stiffener is inserted into the intravesical-pressure channel (the one that has the more forward or intravesical orifice). Pressure-measurement apparatus is then connected to the latter channel after the stiffener is removed.

It is to be understood that all of the foregoing detailed descriptions are by way of example only, and not to be taken as limiting the scope of my invention—which is expressed only in the appended claims.

In particular, my invention encompasses alternative means for anchoring the tube within a patient's urethra. In the course of developing my invention I have studied and experimented with several such approaches, and I consider them within the scope of my invention although the inflatable sliding bougie discussed above seems far preferable.

For example, in the prior art a balloon inflated within a patient's bladder is sometimes used to hold the tip of a catheter inside the bladder. A similar balloon with a short, slender tether to the tip of a catheter tube could be used to hold the catheter tip in a position slightly withdrawn from the bladder. Such a tether would probably irritate the urethra severely—especially if any significant amount of tension were applied to the rearward end of the tube—and therefore would likely throw off the measurements substantially.

A balloon inflated within the urethra itself, generally at the position of the bougie as described above, could also be used to anchor the tube. The balloon would have to slide along the tube, however, and when inflated it would be somewhat traumatic to the urethra.

The apparatus of my invention may also include a needle, extension tube and pressure meter for obtaining a pressure measurement through the abdominal wall, in the case of those patients who can tolerate such a procedure.

I claim:

1. A method for diagnosis of incontinence in a woman by investigating movement of liquid from her bladder to her urethra, comprising the steps of:

positioning a tube partly within such urethra, with the proximal end of the tube at least slightly withdrawn from such bladder and the distal end of the tube extending outwardly through such urethra to the outside of such woman's body;

anchoring the tube, in the position described, by anchoring means positioned within such woman's body:

while the tube is so disposed, causing the woman to undergo stress of a type which induces such incontinence; and observing the timing of discharge of such liquid relative to incidence of the stress.

2. The method of claim 1, wherein the positioning step comprises:

inserting the tube completely through such urethra into such bladder, as determined by observation of the initiation of substantially continuous flow of liquid outwardly from the bladder through the tube to the distal end of the tube; and then withdrawing the tube to the aforesaid position in which the proximal end of the tube is slightly withdrawn from the bladder, as determined by observation of the cessation of said substantially continuous liquid flow.

3. The method of claim 1, also comprising:

measuring pressure within such bladder and observing the timing of changes in such bladder pressure relative to discharge of such liquid and incidence of the stress.

4. The method of claim 3:

also comprising, before the pressure-measuring step, the additional step of inserting a hollow needle through such woman's abdomen into her bladder; and wherein the pressure-measuring step comprises measuring the pressure of fluid at the distal end of the needle.

5. A method for diagnosis of incontinence in a woman by investigating movement of liquid from her bladder to her urethra, comprising the steps of:

positioning a tube partly within such urethra, with the proximal end of the tube at least slightly withdrawn from such bladder and the distal end of the tube extending outwardly through such urethra to the outside of such woman's body;

anchoring the tube, in the position described, by anchoring means positioned within such woman's body;

while the tube is so disposed, causing the woman to undergo stress of a type which induces such incontinence; and observing the timing of discharge of such liquid relative to incidence of the stress;

wherein the anchoring step comprises the substeps of:

sliding an anchoring element around and along the tube from the distal end of the tube into such urethra, and then causing the anchoring element to enlarge radially, relative to the tube, against the interior of such urethra.

6. The method of claim 1, wherein:

the anchoring element comprises a spongelike material that expands at least several-fold upon absorption of liquid; and the enlargement-causing substep comprises bringing a suitable quantity of liquid into contact with the spongelike material.

7. The method of claim 5, wherein the anchoring step comprises the substeps of:

inserting a guide element into such woman's urethral meatus; and inserting an anchoring element through the guide element into the urethra.

8. The method of claim 5, wherein:

the positioning step comprises inserting a guide element into such woman's urethral meatus, and inserting the tube through the guide element into the urethra; and the sliding substep comprises, while the tube is inserted through the guide element into the urethra, sliding the anchoring element along the tube and through the guide element into the urethra.

9. A method for diagnosis of incontinence in a woman by investigating movement of liquid from her bladder to her urethra, comprising the steps of:

positioning a tube partly within such urethra, with the proximal end of the tube at least slightly withdrawn from such bladder and the distal end of the tube extending outwardly through such urethra to the outside of such woman's body;

anchoring the tube, in the position described, by anchoring means positioned within such woman's body;

while the tube is so disposed, causing the woman to undergo stress of a type which induces such incontinence; and observing the timing of discharge of such liquid relative to incidence of the stress;

wherein the positioning step comprises the substeps of:

inserting a guide element into such woman's urethral meatus, and inserting an anchoring element through the guide element into the urethra.

10. The method of claim 9, also comprising:

after the guide-element-inserting substep, causing such woman to grasp the guide element by means of a handle provided thereon, to stabilize the guide element while facilitating access to the urethral meatus for the anchoring step.

11. The method of claim 9:

also comprising, before the pressure-measuring step, inserting a second tube through such urethra into such bladder; and wherein the pressure-measuring step comprises measuring the pressure of fluid at the distal end of the second tube.

* * * * *